US009121010B1

(12) United States Patent
Larocco et al.

(10) Patent No.: US 9,121,010 B1
(45) Date of Patent: Sep. 1, 2015

(54) CONTINUOUS PORCINE KIDNEY CELL LINE CONSTITUTIVELY EXPRESSING BOVINE $\alpha_V\beta_6$ INTEGRIN WITH INCREASED SUSCEPTIBILITY TO FOOT AND MOUTH DISEASE VIRUS (71) Applicant: The United States of America, as Represented by the Secretary of Agriculture, Washington, DC (US)

(72) Inventors: Michael A Larocco, Mattituck, NY (US); Barry Baxt, Valley Stream, NY (US); Hernando Duque, Greenport, NY (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 217 days.

(21) Appl. No.: 13/662,104

(22) Filed: Oct. 26, 2012

(51) Int. Cl.
C12N 15/85 (2006.01)
G01N 33/53 (2006.01)
C12N 5/071 (2010.01)

(52) U.S. Cl.
CPC .......... C12N 5/0684 (2013.01); C12N 2510/00 (2013.01)

(58) Field of Classification Search
None
See application file for complete search history.

(56) References Cited

U.S. PATENT DOCUMENTS

2004/0071659 A1* 4/2004 Chang et al. .................. 424/93.2
2008/0176962 A1* 7/2008 Cohen et al. ................... 514/789

OTHER PUBLICATIONS

Duque et al. Foot-and-mouth disease virus receptors: comparison of bovine alpha(V) integrin utilization by type A and O viruses. J Virol. Feb. 2003;77(4):2500-11.*
Rhodes et al. Mammalian expression of transmembrane receptors for pharmaceutical applications. Biochem Soc Trans. Nov. 1998;26(4):699-704.*

* cited by examiner

Primary Examiner — Michelle S Horning
(74) Attorney, Agent, or Firm — John D. Fado; Evelyn M. Rabin (57) ABSTRACT Foot and out disease virus (FMDV) is worldwide problem. Rapid isolation, serotyping and vaccine matching of FMDV from infected animals is critical to enable the implementation of effective vaccination programs and to stop the spread of infection during outbreaks. Current virus isolation protocols use primary cells, known to be susceptible to FMDV, or baby hamster kidney cells (BHK-21) and other cell lines that are not highly sensitive to some strains of FMDV. The $\alpha_V\beta_6$ integrin is a principal receptor for FMDV. We therefore transduced the porcine kidney cell line, LFBK, to stably express both the $\alpha_V$ and $\beta_6$ bovine integrin subunits. The LFBK-$\alpha_V\beta_6$ cell line showed both $\beta_6$ expression and enhanced susceptibility to FMDV infection for at least 100 cell passages. LFBK-$\alpha_V\beta_6$ cells are highly sensitive for detecting all serotypes of FMDV from experimentally infected animals, including the porcinophillic strain O/TAW/97 and are thus a sensitive tool for FMDV isolation.

11 Claims, 3 Drawing Sheets
(1 of 3 Drawing Sheet(s) Filed in Color)

CONTINUOUS PORCINE KIDNEY CELL LINE CONSTITUTIVELY EXPRESSING BOVINE $\alpha_v\beta_6$ INTEGRIN WITH INCREASED SUSCEPTIBILITY TO FOOT AND MOUTH DISEASE VIRUS

BACKGROUND OF THE INVENTION

1. Field of the Invention

The invention relates to a transgenic cell line which has been engineered to constitutively express the $\alpha_v\beta_6$ integrin receptor, a principal bovine receptor for Foot and Mouth Disease Virus (FMDV). In particular, the invention relates to the transgenic fetal porcine kidney cell line, LFBK $\alpha_v\beta_6$, which is useful for the rapid and sensitive detection and identification of FMDV in diagnostic settings and also to identify serotypes and subtypes thereby facilitating vaccine selection procedures. LFBK $\alpha_v\beta_6$ is highly sensitive and permissive to infection by animal-derived FMDV from all seven serotypes in cell culture. The invention further relates to the transgenic LFBK $\alpha_v\beta_6$ cells for detection of FMDV from field samples.

2. Description of the Relevant Art

Foot and mouth disease virus (FMDV) is a severe economic concern for meat producing nations since the trade of animal products is prohibited from countries where the virus is confirmed. The rapid spread of the virus among susceptible animals results in severe morbidity and in some cases death, especially in young animals (Grubman and Baxt. 2004. *Clin. Microbiol. Rev.* 17: 465-493). Foot and mouth disease (FMD) is an extremely contagious viral disease of cloven-hoofed ungulates which include domestic animals (cattle, pigs, sheep, goats, and others) and a variety of wild animals. Infection or vaccination with one of the seven different serotypes does not confer cross-protection to other serotypes or even some subtypes of the same serotype. Vaccines for FMDV are widely used to prevent clinical disease, but since vaccines are serotype and subtype-specific, the virus(es) causing outbreaks must be isolated and serologically characterized for vaccine matching prior to selecting the appropriate vaccine antigen (reviewed in Rodriguez and Gay. 2011. *Expert Rev. Vaccines* 10:377-387).

Although molecular techniques such as PCR (polymerase chain reaction) coupled with genomic sequencing can be used in samples containing enough virus to rapidly identify the virus serotype and its relationship to other FMDV strains, appropriate vaccine prediction requires virus growth in cell culture to carry out neutralization tests using reference sera. Inefficient recovery of virus from animal samples can delay diagnosis and vaccine selection and thereby hamper rapid implementation of control measures; therefore, virus isolation protocols are designed for maximum sensitivity. Some primary cells, such as bovine thyroid (BTY) cells, are highly susceptible to a wide range of FMDV serotypes (Snowdon, W. A. 1966. *Nature* 210:1079-1080); however, they are difficult and costly to prepare and lose FMDV susceptibility after multiple passages (House and Yedloutschnig. 1982. *Can. J. Comp. Med.* 46:186-189). Primary lamb kidney (LK) cells are also very sensitive to FMDV. Unlike BTY cells, LK cells maintain their sensitivity to FMDV infection after cryopreservation; however, their sensitivity decreases after passage (House and House. 1989. *Vet. Microbiol.* 20:99-109). Immortalized cell lines (e.g. baby hamster kidney (BHK) fibroblasts and porcine kidney epithelial cells), while much easier to maintain, are in many cases less susceptible to specific animal-derived FMDV serotypes (Swaney, L. M. 1976. *Amer. J. Vet. Res.* 37:1319-1322; Ferris et al. 2006. *Vet. Microbiol.* 117:130-140; Ferris et al. 2002. *Vet. Microbiol.* 84:307-316; De Castro, M. P. 1964. *Arch. Inst. Biol. San Paulo* 31: 63-78).

Integrins of the $\alpha_v$ subgroup have been demonstrated to be FMDV receptors by several laboratories including ours (Ruiz-Saenz et al. 2009. *Intervirol.* 52:201-212). Of the many $\alpha_v$ integrins that have been shown to mediate FMDV attachment, the integrin $\alpha_v\beta_6$ has been shown to be one of the most efficient receptors for all FMDV serotypes (Jackson et al. 2000. *J. Virol.* 74:4949-4956; Ferris et al. 2005. *J. Virological Methods* 127:69-79) and high levels of $\alpha_v\beta_6$ expression are observed on epithelial cells at the sites of infection in cattle and swine (Monaghan et al. 2005. *J. Gen. Virol.* 86:2769-2780; O'Donnell et al. 2009. *J. Comp. Path.* 141:98-112). BTY cells, considered the most sensitive primary cells for FMDV isolation, have high levels of $\alpha_v\beta_6$ integrin surface expression (King et al. 2011. *Vet. Immunol. Immunopath.* 140:259-265). Moreover, transient expression of bovine $\alpha_v$ and $\beta_6$ integrin subunits in baby hamster kidney cells (BHK3-$\alpha_v\beta_6$) (Duque et al. 2004. *J. Virol.* 78:9773-9781) greatly increased the susceptibility of this cell line to a cow-passaged A24 Cruziero strain that contains an SGD motif in the VP1 (FMD Virus Protein 1) capsid protein (Rieder et al. 2005. *J. Virol.* 79:12989-12998). Although the BHK3-$\alpha_v\beta_6$ cells were initially more permissive to the A24-SGD virus than BHK-21 cells were, the BHK3-$\alpha_v\beta_6$ cells lost integrin expression and sensitivity to the A24-SGD virus after multiple passages (E. Rieder, personal communication).

Swaney derived an immortalized line of fetal porcine kidney (LFBK) cells that had high susceptibility to most FMDV serotypes and the susceptibility was maintained over many passages (Swaney, L. M. 1988. *Vet. Microbiol.* 18:1-14). Compared to BTY cells, LFBK cells had similar susceptibility to most FMDV serotypes and had equal or better susceptibility than the MVPK (Mengeling-Vaughn Porcine Kidney) cell line, the porcine kidney cell line, IB-RS-2, and fetal bovine kidney cells in the same experiments.

There is a need for a cell line that is easily maintained and is highly susceptible to all serotypes and subtypes of FMDV. The present invention, described below, combines the long-lived FMDV susceptibility of the LFBK cell line with a principal bovine receptor for FMDV, the $\alpha_v\beta_6$ integrin receptor, to provide a stable cell line which is highly susceptible to FMDV.

SUMMARY OF THE INVENTION

We have developed and characterized a stable transgenic cell line that is highly susceptible to animal-derived FMDV from all seven serotypes and discovered that this cell line greatly facilitates FMDV isolation and growth from field samples ensuring more accurate and more rapid diagnosis of the FMDV serotype involved in an outbreak, when compared to other cells used for diagnosis.

In accordance with this discovery, it is an object of the invention to provide the transgenic fetal porcine kidney cell line, LFBK $\alpha_v\beta_6$, engineered to express the $\alpha_v\beta_6$ integrin receptor, a principal bovine receptor for FMDV.

It is a further object of the invention to provide LFBK $\alpha_v\beta_6$ cells for the rapid isolation and growth of FMDV serotypes and subtypes from field samples thereby facilitating vaccine selection procedures. LFBK $\alpha_v\beta_6$ is sensitive and permissive to infection by animal-derived FMDV from all seven serotypes in cell culture.

It is another object of the invention to provide LFBK $\alpha_v\beta_6$ cells for the rapid and sensitive detection and identification of all seven serotypes of FMDV and multiple subtypes from field samples thereby facilitating vaccine selection procedures.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 1A-1F depict LFBK-$\alpha_v\beta_6$ cell characterization. FIG. 1E depicts the relationship between susceptibility and time after seeding. Cells were seeded at the indicated time prior to infection then infected with serial dilutions of the indicated virus for titer determination as described in Example 1.

FIG. 2 illustrates the susceptibility of 6 cell types to animal-derived FMDV. Cells were infected with the indicated viruses and virus titers were determined for each cell type as described in Example 2. Each solid line is the axis for data generated from the indicated virus strain. Colored points on the solid lines indicate the mean titer of that virus strain in a single cell type (Refer to Table 2 for sample range). Dashed lines specify the $\log_{10}$ scale of the virus titer in PFU/ml; points located on the outside of the plot correspond to higher virus titers ($10^8$) than those located toward the center ($10^2$).

FIGS. 3A and 3B depict detection of FMDV in diagnostic samples. Wells of 48-well plates seeded with the indicated cells were infected with 38 FMDV-suspect tissue homogenates from Afghanistan, Bolivia and Pakistan (see Table 3 for isolate information). Beginning at 4 hours post infection, each well was scored for the presence of cytopathic effects (CPE). In FIG. 3A, each point on the scatter plot represents the time after infection that a cytopathic effect was first detected in a given well for one diagnostic isolate. "NC" denotes the diagnostic samples that did not induce visible cytopathic effects by 48 hours in the indicated cells. In FIG. 3B, each point on the graph represents the average CPE score for all 38 diagnostic isolates at each time point. 1+, up to 25% of the cell monolayer exhibited visual CPE; 2+, approximately 50% of the cell monolayer exhibited CPE; 3+, approximately 75% of the cell monolayer exhibited CPE; 4+, 100% of the cell monolayer exhibited CPE.

DETAILED DESCRIPTION OF THE INVENTION

Here we report the engineering and comprehensive characterization of the LFBK-$\alpha_v\beta_6$ cell line, a fetal porcine kidney cell line stably transduced with the bovine $\alpha_v$ and $\beta_6$ integrin subunits. The expression of the $\beta_6$ integrin subunit and the resulting enhanced infectivity of FMDV containing a SGD domain in VP1 were both maintained for at least 100 cell passages. We found that the LFBK-$\alpha_v\beta_6$ cells were more susceptible to all FMDV serotypes derived from experimentally-infected animals as compared to the LFBK cells from which they were derived and other cells commonly used for FMDV isolation. In a diagnostic sensitivity assay, LFBK-$\alpha_v\beta_6$ cells were more sensitive than primary lamb kidney cells, the porcine kidney cell line IB-RS-2, and the BHK cell line. LFBK-$\alpha_v\beta_6$ cells were also able to detect other vesicular disease viruses. Our results support the use of LFBK-$\alpha_v\beta_6$ cells for FMDV diagnostic purposes.

Figure 2:
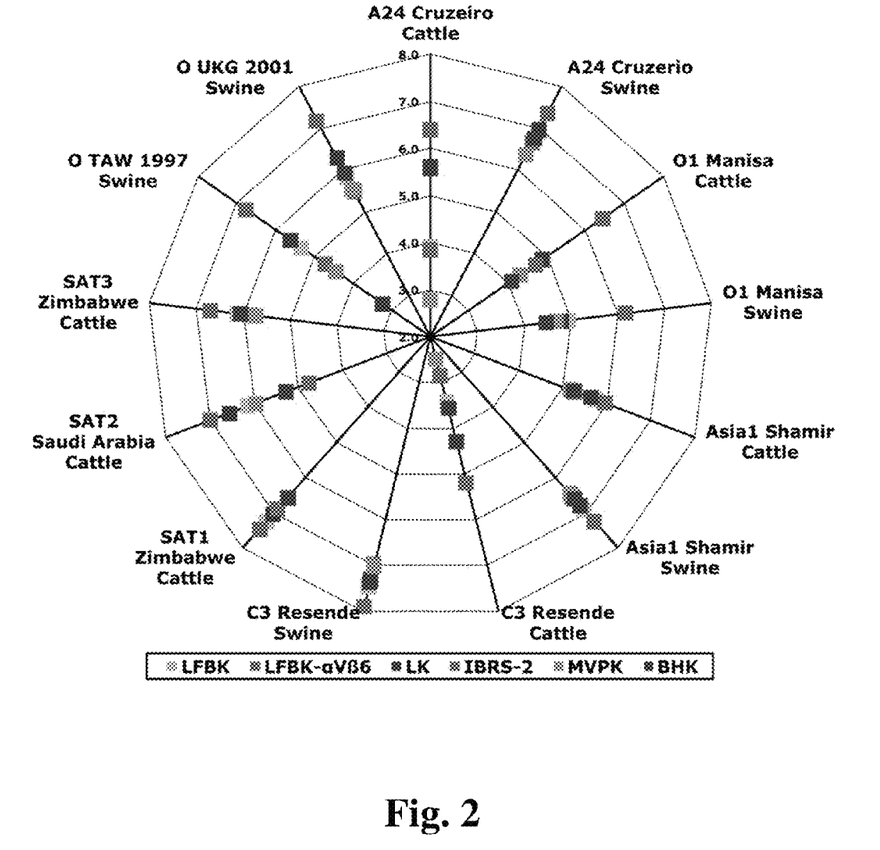

Our data indicate that the LFBK-$\alpha_v\beta_6$ cells are excellent for detecting FMDV serotype O isolates. A previous study at PIADC (Plum Island Animal Disease Center) showed that LFBK cell sensitivity to O1 Manisa isolated from cattle was close to the $ID_{50}$ observed in primary bovine tongue cells (Pacheco et al. 2010. Vet. J. 183:46-53); however, we have observed that the transgenic LFBK-$\alpha_v\beta_6$ cells detect O1 Manisa over one $\log_{10}$ more efficiently than LFBK cells. Further, Burman and coworkers showed that the integrin-binding domain on the VP1 capsid protein from O1 FMDV binds $\alpha_v\beta_6$ with the highest affinity among the $\alpha_v\beta_3$, $\alpha_v\beta_6$ and $\alpha_v\beta_8$ integrins (Burman et al. 2006. J. Virol. 80:9798-9810). In addition, in our experiments (FIG. 2), O1 Manisa viruses are detected at a level almost two logs better in LFBK-$\alpha_v\beta_6$ cells than in IB-RS-2 cells that do not express the high levels of $\alpha_v\beta_6$ (King et al., supra).

BHK-21 cells are widely used for FMDV virus isolation, due to their rapid growth properties and sufficient susceptibility to most serotypes of FMDV. BHK cells generally performed very well in our sensitivity experiments (FIG. 2), detecting cattle-derived A24 with the same sensitivity as primary LK cells; O1 Manisa (from both swine and cattle) was the only serotype where BHK had the least efficient FMDV detection of the cell lines tested. In our diagnostic experiments (FIG. 3A), the use of low-passage BHK cells was able to eventually detect FMDV from 18 out of 40 diagnostic tissue samples and in five cases, the detection of a few single infected BHK cells by immunohistochemistry. Taken together, our results with BHK cells clearly indicate that they are not as susceptible to animal-derived isolates as LFBK-$\alpha_v\beta_6$ cells.

FMDV strain O/TAW/97 does not grow well in primary bovine thyroid cells (BTY) or in cattle; yet, O/TAW/97 grows in the IB-RS-2 porcine kidney cell line and is extremely virulent in swine (Dunn and Donaldson. 1997. Vet. Rec. 141:174-175). As such, O/TAW/97 has been referred to as a "porcinophillic" virus (Dunn and Donaldson, supra; Knowles et al. 2001. J. Virol. 75:1551-1556; Pacheco and Mason. 2010. J. Vet. Sci. 11:133-142). In our experiments this virus also grew poorly in primary lamb kidney cells, forming extremely small plaques. However, O/TAW/97 grew better in the porcine-derived LFBK cells than in the cell lines of swine origin, namely, MVPK and IB-RS-2. The expression of $\alpha_v\beta_6$ in the LFBK-$\alpha_v\beta_6$ cells enhanced infectivity of the O/TAW/97 virus over the infectivity levels observed in LFBK cells to a level about the same as seen with the O1 Manisa and O/UKG/2001 viruses.

LFBK-$\alpha_v\beta_6$ cells have been in use at PIADC for all aspects of FMDV virology with tremendous success. They support the replication of animal-derived virus strains that do not grow well in other cell types (e.g. O1 Manisa, O/TAW/97) and maintain high sensitivity to FMDV for at least 100 subculture passages. They do not require the extraction of animal organs to make primary cells, they grow as efficiently as standard LFBK cells, and they have no special media requirements. We have characterized the FMDV susceptibility of this transduced cell line by infection with animal-derived FMDV from all 7 serotypes as well as recent diagnostic field samples and compared its susceptibility to that of other cell types used for diagnostic FMDV virus isolation. Our results indicate that LFBK-αvβ6 cells are highly permissive for all FMDV serotypes and have excellent performance in a diagnostic setting. Based on the data presented here, LFBK-$α_vβ_6$ cells are a valuable tool for the rapid detection and/or isolation of FMDV serotypes in clinical laboratories and are exceptionally suited for all routine FMDV diagnostic and research-based cell applications.

The terms "sample" and "specimen" in the present specification and claims are used in their broadest sense to include any composition that is obtained and/or derived from biological or environmental source, as well as sampling devices (e.g., swabs) which are brought into contact with biological or environmental samples. "Biological samples" include those obtained from an animal, including cloven-hoofed ungulates which include domestic animals (cattle, pigs, sheep, goats, and others) and a variety of wild animals, body fluids such as urine, blood, fecal matter, cerebrospinal fluid (CSF), semen, sputum, and saliva, as well as solid tissue. Also included are samples obtained from food products and food ingredients such as dairy items, meat, meat by-products, and waste. "Environmental samples" include environmental material such as surface matter, soil, water, and industrial materials, as well as material obtained from food and dairy processing instruments, apparatus, equipment, disposable, and non-disposable items. These examples are not to be construed as limiting the sample types applicable to the present invention.

As used herein, the term "cell type," refers to any cell, regardless of its source or characteristics.

As used herein, the term "microorganism" refers to any organism of microscopic or ultramicroscopic size including, but not limited to, viruses, bacteria, and protozoa.

As used herein, the term "culture" refers to a composition, whether liquid, gel, or solid, which contains one or more microorganisms and/or one or more cells. A culture of organisms and/or cells can be pure or mixed. For example, a "pure culture" of an organism as used herein refers to a culture in which the organisms present are of only one strain of a single species of a particular genus. This is in contrast to a "mixed culture" of organisms which refers to a culture in which more than one strain of a single genus and/or species of microorganism is present.

As used herein, the terms "culture media," and "cell culture media," refer to media that are suitable to support maintenance and/or growth of cells in vitro (i.e., cell cultures).

A "primary cell" is a cell which is directly obtained from a tissue or organ of an animal whether or not the cell is in culture.

A "cultured cell" is a cell which has been maintained and/or propagated in vitro. Cultured cells include primary cultured cells and cell lines.

"Primary cultured cells" are primary cells which are in in vitro culture and which preferably, though not necessarily, are capable of undergoing ten or fewer passages in in vitro culture before senescence and/or cessation of proliferation.

The terms "cell line" and "immortalized cell" refer to a cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells.

Cell lines may be generated spontaneously or by transformation. A "spontaneous cell line" is a cell line which arises during routine culture of cells. A "transformed cell line" refers to a cell line which is generated by the introduction of a "transgene" comprising nucleic acid (usually DNA) into a primary cell or into a finite cell line by way of human intervention Cell lines include, but are not limited to, finite cell lines and continuous cell lines. As used herein, the term "finite cell line" refers to a cell line which is capable of a limited number of cell divisions prior to senescence.

The term "continuous cell line" refer to a cell line which is capable of more than about 50 (and more preferably, an infinite number of) cell divisions.

The term "transgene" is understood to describe genetic material which has been or is about to be artificially inserted into the genome of a non-human animal, and particularly into a cell of a living non-human mammal. It is to be understood that as used herein the term "transgenic" includes any cell, cell line, or tissue, the genotype of which has been altered by the presence of a heterologous nucleic acid. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed.

The term "transduction" is used to refer to the introduction of genetic material into a cell by using a viral vector. As used herein a transduced cell results from a transduction process and contains genetic material it did not contain before the transduction process, whether stably integrated or not.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell Host organisms containing the transformed nucleic acid fragments are referred to as "transgenic" organisms. Thus, isolated polynucleotides can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" refers to a recombinant nucleic acid, generally recombinant DNA, that has been generated for the purpose of the expression of a specific nucleotide sequence(s), or is to be used in the construction of other recombinant nucleotide sequences. A "chimeric gene construct" refers to a nucleic acid sequence encoding a protein, operably linked to a promoter and/or other regulatory sequences.

As used herein, the term "express" or "expression" is defined to mean transcription alone. "Altered levels" or "altered expression" refers to the production of gene product (s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters".

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

As used herein, the term "FMD" encompasses disease symptoms in cattle and swine caused by a FMDV infection. Examples of such symptoms include, but are not limited to, vesicles in the mouth, and on the feet. As used herein, a FMDV that is "unable to produce FMD" refers to a virus that can infect a pig, but which does not produce any disease symptoms normally associated with a FMD infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The terms "foot and mouth disease virus" and "FMDV", as used herein, unless otherwise indicated, mean any strain of FMD viruses.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly bovine and porcine cells, and are described in further detail below.

A "functional virion" is a virus particle that is able to enter a cell capable of hosting a FMDV, and express genes of its particular RNA genome (either an unmodified genome or a genetically modified genome) within the cell.

In summary, we provide a stable transgenic fetal porcine kidney cell line, LFBK $\alpha_v\beta_6$, useful for the rapid isolation and sensitive detection and identification of all seven FMDV serotypes and multiple subtypes in cell culture. The invention provides for highly sensitive detection of FMDV from field samples.

EXAMPLES

Having now generally described this invention, the same will be better understood by reference to certain specific examples, which are included herein only to further illustrate the invention and are not intended to limit the scope of the invention as defined by the claims.

Example 1

LFBK Cells Expressing Bovine $\alpha_v\beta_6$ Integrin: Growth and Characterization LFBK cells were propagated in DMEM supplemented with 10% fetal bovine serum and antibiotics as previously described (Piccone et al. 2009. *J. Virol.* 83:6681-6688) and used for these experiments between passages 64 and 71. LFBK-$\alpha_v\beta_6$ cells were propagated in the same manner as LFBK cells and used at the passage indicated in each experiment. BHK cells, used between passages 62 and 67, were propagated in MEM supplemented with 10% calf serum, 10% tryptose phosphate broth and antibiotics. Primary lamb kidney (LK) cells, generously supplied by the APHIS Diagnostic Service Section at PIADC, were propagated in DMEM supplemented with 10% fetal bovine serum, antibiotics and sodium pyruvate and used directly from cryovials or at passage 1 as indicated. IB-RS-2 cells were used between passage 129 and 137 and MVPK cells were used between passages 38 and 41; both of these cell lines were propagated in MEM supplemented with 10% fetal calf serum, nonessential amino acids and antibiotics.

The integrin $\alpha_v\beta_6$ is an important receptor for FMDV in relevant tissues in vivo. LFBK cells are a transformed cell line that has high sensitivity to most FMDV serotypes but does not express high levels of $\beta_6$ integrin protein. In order to merge the enhanced susceptibility of $\alpha_v\beta_6$ expression with the transformed phenotype of LFBK cells, the bovine $\alpha_v$ and $\beta_6$ integrin subunits were transduced into LFBK cells. Individual retroviruses expressing the bovine $\alpha_v$ (Gen Bank AF239958) or bovine $\beta_6$ (GenBank AF468060) integrin subunits (Duque et al., supra) were created with the Pantropic Retroviral Expression System (Clontech PT3346-5) following the manufacturer's protocol. LFBK cells at passage 145 were infected with the $\alpha_v$-expressing retrovirus and neomycin selection was used to select against non-transduced cells. A pool of these cells was infected with the $\beta_6$-expressing retrovirus, then cloned to single cells by terminal dilution. Clones were chosen that showed consistent expression of the $\beta_6$ subunit by immunohistochemistry.

Immunohistochemical staining was used to demonstrate the long-term maintenance of $\beta_6$ expression in LFBK-$\alpha_v\beta_6$ cells. The Vectastain ABC kit (Vector Labs, PK-6102) and Vector VIP peroxidase substrate kit (Vector Labs, SK-4600) were used according to the manufacturer's protocols. Mouse anti-human $\beta_6$ (Chemicon, CSb6) was used to detect the bovine integrin subunit $\beta_6$ at a 1:300 dilution. The mouse monoclonal antibody F19-51 (Yang et al. 2007. *J. Immunol. Methods* 321:174-181) was used to detect the FMDV 3D protein at a 1:200 dilution.

Figure 1A:
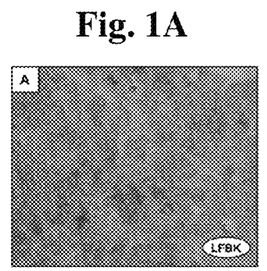
FIGS. 1A-1C show that LFBK-$\alpha_v\beta_6$ cells maintain long-term expression of $\beta_6$. Mouse anti-human $\beta_6$ (Chemicon, CSb6) was used to detect the bovine integrin subunit $\beta_6$.
Figure 1B:
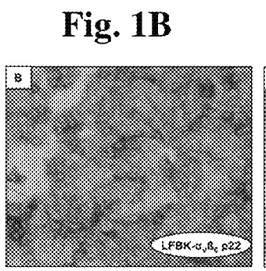
Figure 1C:
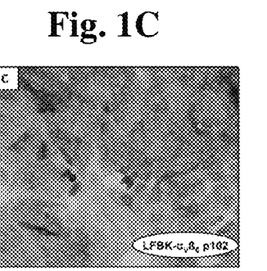

Immunohistochemical staining demonstrated the long-term maintenance of $\beta_6$ expression in the LFBK-$\alpha_v\beta_6$ cells for at least 102 cell passages as compared to the non-transduced LFBK cells (FIG. 1A-C).

FMDV A24-SGD, an FMDV A24 Cruziero strain serially passed in cattle, has an SGD motif in the G-H loop of VP1 and enhanced infectivity in cells expressing the $\alpha_v\beta_6$ integrin (Rieder et al., supra). LFBK-$\alpha_v\beta_6$ cells at various subculture passages and non-transduced LFBK cells were infected with A24-SGD or a cell culture grown control virus (A24-BHK) to confirm the long-term functional maintenance of the $\alpha_v\beta_6$ integrin.

Cells were seeded 72 hours before infection in 6-well cell culture plates unless otherwise noted. Inoculum volume was 200 µl. 1 hour post adsorption, the inoculum was removed and the cells were overlaid with 50/50 1.2% Gum Tragacanth/2× MEM supplemented with antibiotic/antimycotic. Plates were incubated for 24 hours unless otherwise indicated then simultaneously fixed and stained with Histo-Choice tissue fixative (AMRESCO) containing crystal violet and plaques were counted.

Figure 1D:
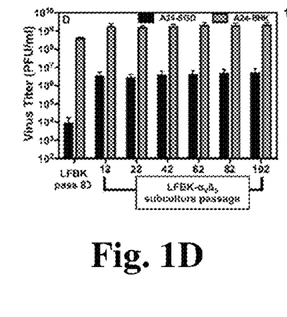
FIG. 1D shows that LFBK-$\alpha_v\beta_6$ cells maintain long-term susceptibility to A24-SGD. The indicated cells were infected with serial dilutions of either A24-BHK or A24-SGD for plaque determination as described in Example 1.
Figure 1E:
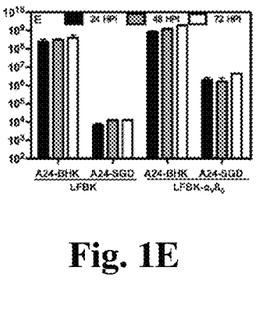

The results of these experiments showed that the LFBK-$\alpha_v\beta_6$ cells have a 2.5 log increased susceptibility to A24-SGD compared to LFBK cells and that the increased susceptibility is maintained for over 100 passages (FIG. 1D). Expression of surface proteins can be delayed due to trypsin treatment during cell subculturing. To determine if increasing the time between seeding and infecting the cells had an effect on susceptibility, LFBK and LFBK-$\alpha_v\beta_6$ cells were seeded on plates 24, 48 or 72 hours prior to infection with A24-SGD or A24-BHK viruses. It was found that seeding the LFBK-$\alpha_v\beta_6$ cells 72 hours prior to infection provided only slightly better sensitivity than seeding 24 hours prior to infection (FIG. 1E). This result indicates that the LFBK-$\alpha_v\beta_6$ cells can be infected early after subculturing with only minimal loss of susceptibility.

Figure 1F:
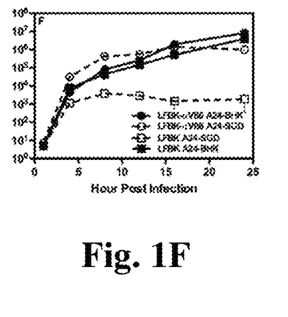
FIG. 1F is a comparison of FMDV A24-BHK and A24-SGD growth in LFBK and LFBK-$\alpha_v\beta_6$ cells. LFBK and LFBK-$\alpha_v\beta_6$ cells were seeded in 24-well plates and infected 72 hours later with either A24-BHK or A24-SGD at MOI=0.01. After 1 hour, the monolayers were acid washed and fresh media was added. At the indicated time after infection, the plates were frozen at −70° C., thawed and titrated on LFBK-$\alpha_v\beta_6$ cells.

In order to show that the LFBK-$\alpha_v\beta_6$ cells support the normal growth progression of FMDV, a multi-step growth curve was performed (FIG. 1F). LFBK-$\alpha_v\beta_6$ or LFBK were seeded in 24 well plates 72 hours before infection with either FMDV A24-BHK (a cell culture-passaged virus containing the wild-type RGD motif in VP1) or FMDV A24-SDG (vesicular fluid from the second bovine passage of the SGD-containing A24-B9 virus described in (Rieder et al., supra) at a multiplicity of 0.01 PFU/cell. The viruses were absorbed for 1 hour with rocking at 37° C. The cells were then acid washed (25 mM MES pH 5.5 in 145 mM NaCl), washed once with growth media, and incubated at 37° C. in 0.5 mL growth media per well. At the indicated time, cells were frozen at −70° C., thawed and virus titer was determined by plaque assay on LFBK-αvβ6 cells.

In this experiment, the replication of A24-BHK was similar in both LFBK and LFBK-$\alpha_v\beta_6$ cells. While A24-SGD replicated slowly in the non-transduced LFBK cells, this virus grew normally in LFBK-$\alpha_v\beta_6$ cells, demonstrating that the expression of $\alpha_v\beta_6$ in LFBK cells complements the defect of non-transduced LFBK cells to support efficient A24-SGD replication.

Example 2

Susceptibility of LFBK-αVβ6 Cells to Animal-Derived FMDV of all Serotypes

In order to determine the susceptibility of LFBK-$\alpha_v\beta_6$ cells to animal-derived FMDV strains and compare with that of LFBK, primary lamb kidney (LK), BHK, and two swine kidney cells lines (IB-RS-2 and MVPK), each cell type was infected with serial dilutions of infected tissue macerates or vesicular fluid obtained from animals experimentally infected with each of the FMDV serotypes. The viruses used in this experiment are listed in Table 1.

TABLE 1

Animal-derived viruses used in this study.

| Virus | Sample Species | Sample Type |
|---|---|---|
| A24 Cruzeiro | swine | Vesicular Fluid (VF) |
| A24 Cruzeiro | bovine | Pool of Tongue Tissue Homogenate and Vesicular Fluid |
| O1 Manisa | bovine | Vesicular Fluid |
| O1 Manisa | swine | Vesicular Fluid |
| Asia1 Shamir | bovine | Tongue Tissue Homogenate |
| Asia1 Shamir | swine | Vesicular Fluid |
| C3 Resende | swine | Vesicular Fluid |
| C3 Resende | bovine | Tongue Tissue Homogenate |
| O Taiwan 1997 O/TAW/35/1997 | swine | Vesicular Fluid |
| O UKG UKG/35/2001 | swine | Vesicular Fluid |
| SAT1 Zimbabwe | bovine | Tongue Tissue Homogenate |
| SAT2 SAU2000 | bovine | Vesicular Fluid |
| SAT3 Zimbabwe | bovine | Tongue Tissue Homogenate |

For each strain of virus, the LFBK-$\alpha_v\beta_6$ cells had equal or higher sensitivity to animal-derived FMDV compared to the other cells tested. In some cases, especially with the O serotype FMDV strains, the LFBK-$\alpha_v\beta_6$ cells supported FMDV replication greater than tenfold higher than most cell types tested (FIG. 2) and Table 2.

TABLE 2

Strain Susceptibility of 6 Cell Types to Animal-Derived FMDV Samples.

| Virus Strain (Species) | LFBK-$\alpha_v\beta_6$ | LFBK | LK | IB-RS-2 | MVPK | BHK |
|---|---|---|---|---|---|---|
| A24 Cruzerio (Cattle) | 6.4 ± 0.4[#] | 3.9 ± 0.4 | 5.6 ± 0.1 | 3.9 ± 0.2 | 2.8 ± 0.6 | 5.6 ± 0.7 |
| A24 Cruzerio (Swine) | 7.4 ± 0.2 | 6.9 ± 0.4 | 7.0 ± 0.6 | 6.7 ± 0.4 | 6.4 ± 0.3 | 6.8 ± 0.6 |
| O1 Manisa (Cattle) | 6.4 ± 0.5 | 4.9 ± 0.4 | 4.9 ± 0.8 | 4.7 ± 0.6 | 4.3 ± 0.5 | 4.1 ± 0.6 |
| O1 Manisa (Swine) | 6.2 ± 0.5 | 4.9 ± 0.5 | 4.8 ± 0.5 | 4.7 ± 0.5 | 4.6 ± 0.3 | 4.5 ± 0.2 |
| Asia1 Shamir (Cattle) | 6.0 ± 0.4 | 5.7 ± 0.3 | 5.6 ± 0.3 | 5.3 ± 0.1 | 5.2 ± 0.3 | 5.2 ± 0.2 |
| Asia1 Shamir (Swine) | 7.2 ± 0.2 | 6.9 ± 0.2 | 6.8 ± 0.1 | 6.6 ± 0.3 | 6.5 ± 1.1 | 6.6 ± 0.3 |
| C3 Resende (Cattle) | 5.2 ± 0.6 | 3.4 ± 0.3 | 4.3 ± 0.6 | 2.9 ± 0.4 | 2.5 ± 0.2 | 3.6 ± 0.1 |
| C3 Resende (Swine) | 7.9 ± 0.1 | 7.5 ± 0.4 | 7.3 ± 0.1 | 7.0 ± 0.2 | 7.0 ± 0.7 | 7.4 ± 0.1 |
| SAT1/ZIM (Cattle) | 7.5 ± 0.5 | 7.2 ± 0.4 | 7.0 ± 0.4 | 6.9 ± 0.1 | 6.6 ± 0.8 | 6.6 ± 0.5 |
| SAT2/SAU (Cattle) | 7.0 ± 0.4 | 6.1 ± 0.3 | 6.6 ± 0.7 | 4.8 ± 0.9 | 6.0 ± 0.8 | 5.3 ± 0.5 |
| SAT3/ZIM (Cattle) | 6.7 ± 0.2 | 6.1 ± 0.3 | 5.9 ± 0.3 | 5.8 ± 0.5 | 5.7 ± 0.1 | 6.1 ± 0.5 |
| O/TAW/1997 (Swine) | 6.8 ± 0.6 | 5.3 ± 0.1 | 3.2 ± 0.1 | 4.7 ± 0.1 | 4.4 ± 0.6 | 5.6 ± 0.6 |
| O/UKG/2001 (Swine) | 7.2 ± 0.3 | 5.8 ± 1.4 | 6.3 ± 0.3 | 5.5 ± 0.2 | 5.6 ± 1.0 | 5.9 ± 0.1 |

[#]$\log_{10}$ PFU/ml ± max-min

These data confirm that LFBK-$\alpha_v\beta_6$ cells can readily detect all FMDV serotypes in tissues from experimentally-infected animals.

Example 3

Detection of FMDV in Diagnostic Tissue Samples

LK cells, BHK, IB-RS-2 and LFBK-$\alpha_v\beta_6$ were seeded onto 48-well cell culture plates 48 hours prior to infection. LK cells were seeded directly from storage cryovials. LFBK-$\alpha_v\beta_6$ cells were seeded at passage 32, IB-RS-2 at passage 136 and BHK-21 at passage 66. Diagnostic lesion tissues were disrupted and virus isolated after centrifugation through a Spin-X purification column (Costar) as described in (Pacheco et al. 2010, supra). 100 µl of a 1:10 dilution of these tissue macerates were used to infect each cell type for 1 hour at 37° C. After adsorption, 400 µl of growth media was added to each well and the plates were incubated at 37° C. Starting at 4 HPI, visual evidence of cytopathic effects was recorded every 2 hours until 20 HPI, then at 24, 28 and 48 HPI. At 48 HPI, all wells were fixed with 50% acetone:50% methanol and wells negative for cytopathic effects were immunohistochemically stained with a monoclonal antibody to FMDV 3D protein to confirm negative results.

Samples from experimentally-infected animals tend to be very high titer and have better integrity than field samples. To more closely mimic diagnostic conditions, we obtained field diagnostic samples from Afghanistan, Bolivia and Pakistan (Table 3).

TABLE 3

Field Diagnostic Samples

| Virus Designation | Species |
|---|---|
| A/AFG/156/2005 | Cattle |
| A/AFG/160/2005 | Cattle |
| O/AFG/210/2004 | Cattle |
| O/BOL/741/2000 | Cattle |
| O/BOL/758/2001 | Cattle |
| A/BOL/803/2001 | Cattle |
| A/BOL/812/2001 | Cattle |
| O/Sargodha/PAK/9/2010 | Cattle |
| O/Islamabad/PAK/10/2010 | Cattle |
| O/Bahawalpur/PAK/11/2010 | Cattle |
| O/Bahawalpur/PAK/12/2010 | Buffalo |
| O/Bahawalpur/PAK/13/2010 | Buffalo |
| O/Rawalpindi/PAK/14/2010 | Buffalo |

TABLE 3-continued

Field Diagnostic Samples

| Virus Designation | Species |
|---|---|
| O/Rawalpindi/PAK/15/2010 | Buffalo |
| O/Sahiwal/PAK/16/2010 | Buffalo |
| O/Sargodha/PAK/17/2010 | Buffalo |
| O/Sargodha/PAK/18/2010 | Cattle |
| Asia1/Sargodha/PAK/22/2011 | Cattle |
| Asia1/Sargodha/PAK/23/2011 | Cattle |
| Asia1/Sargodha/PAK/24/2011 | Cattle |
| Asia1/Sargodha/PAK/25/2011 | Cattle |
| Asia1/Sargodha/PAK/26/2011 | Cattle |
| Asia1/Sargodha/PAK/27/2011 | Cattle |
| Asia1/Sargodha/PAK/28/2011 | Cattle |
| Asia1/Sargodha/PAK/29/2011 | Cattle |
| ?/Sargodha/PAK/30/2011 | Cattle |
| Asia1/Karachi/PAK/31/2011 | Buffalo |
| Asia1/Karachi/PAK/32/2011 | Buffalo |
| Asia1/Karachi/PAK/33/2011 | Buffalo |
| O/Karachi/PAK/34/2011 | Buffalo |
| Asia1/Karachi/PAK/35/2011 | Buffalo |
| Asia1/Karachi/PAK/36/2011 | Buffalo |
| Asia1/Karachi/PAK/37/2011 | Buffalo |
| O/Karachi/PAK/38/2011 | Buffalo |
| Asia1/Karachi/PAK/39/2011 | Buffalo |
| O/Karachi/PAK/40/2011 | Buffalo |
| O/Karachi/PAK/41/2011 | Buffalo |
| O/Karachi/PAK/42/2011 | Buffalo |

Figure 3A:
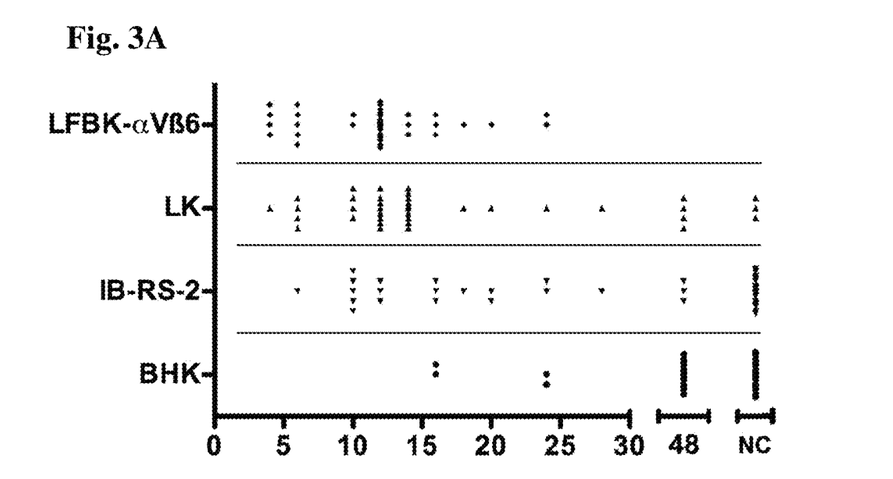

These samples were processed from tissue according to standard virus isolation procedures and used to infect LFBK-$\alpha_v\beta_6$ cells and also other cells commonly used for FMDV diagnostics, including LK, IB-RS-2 and BHK cells. FIG. 3A shows the time point at which each diagnostic isolate first showed visible CPE in each cell line. LFBK-$\alpha_v\beta_6$ was the only cell type in which all clinical samples were detected and scored as CPE positive by 24 h. Few samples yielded virus in all four cell lines. Twelve samples showed CPE in only LFBK-$\alpha_v\beta_6$ and LK cells. Three of the 38 isolates tested only grew in LFBK-$\alpha_v\beta_6$ cells. These data thus show that LFBK-$\alpha_v\beta_6$ cells are the most sensitive to these FMDV field isolates among all the cells tested. In order to rule out the presence of FMDV in non-cytopathic infection, all CPE-negative wells were stained for FMDV 3D antigen after 48 HPI; none of the CPE-negative LK and IB-RS-2 wells reacted with the antibody. 5 CPE-negative BHK wells had individual non-rounded cells that stained positive for antigen (data not shown), indicating these particular FMDV isolates were able to enter BHK cells but not spread efficiently in the culture by 48 h.

Figure 3B:
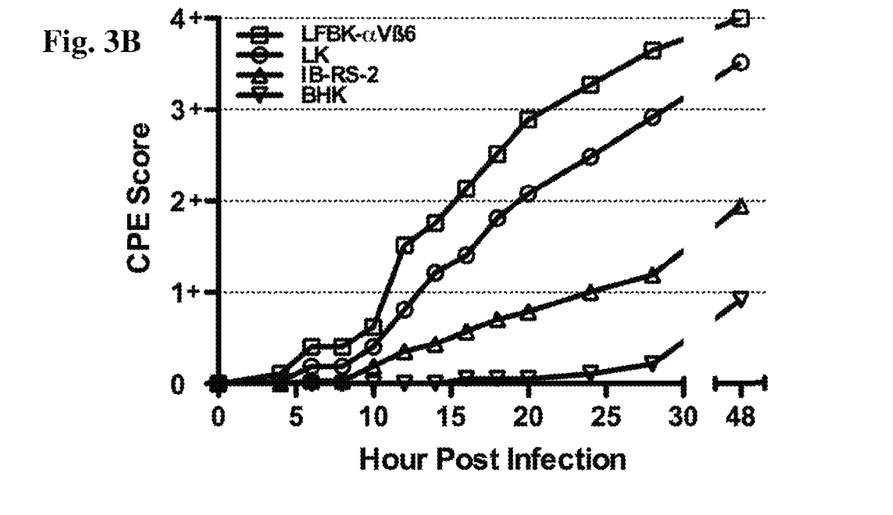

FIG. 3B shows the overall CPE progression over time in all 38 virus isolates by plotting the mean CPE score of each isolate at each time point per cell type. On average, the LK and LFBK-$\alpha$V$\beta$6 cells performed very similarly, both being much more sensitive to the diagnostic isolates than the IB-RS-2 and BHK cells. While the LFBK-$\alpha_v\beta_6$ cells had slightly faster overall early detection of the isolates than the LK cells, the higher mean CPE score at later times indicates a faster progression of virus replication in the LFBK-$\alpha_v\beta_6$ cells. Taken together, the enhanced susceptibility, rapid initial detection of CPE, and faster progression of CPE strongly suggests that LFBK-$\alpha_v\beta_6$ cells are superior to many cells currently used for FMDV diagnostics from tissue specimens.

Example 4

Susceptibility of LFBK-$\alpha$V$\beta$6 Cells to Other Vesicular Disease-Causing Viruses Animals exhibiting vesicular lesions may be infected with other agents besides FMDV. In order to determine if LFBK-$\alpha_v\beta_6$ cells could detect other viruses causing vesicular disease, we inoculated BHK, LK, IB-RS-2, LFBK or LFBK-$\alpha_v\beta_6$ cells with each of 5 non-FMD viruses causing vesicular disease.

We found that vesicular exanthema of swine virus (VESV) and swine vesicular disease virus (SVDV) replicated as well in LFBK-$\alpha_v\beta_6$ cells as they did in IB-RS-2 cells (Table 4). Vesicular stomatitis viruses serotype New Jersey (VSV-NJ) grew to similar titers in all the cell lines. LK, LFBK and LFBK-$\alpha_v\beta_6$ cells supported the growth of bovine papular stomatitis virus (BPSV) as evidenced by the formation of plaques; BPSV grew to a slightly higher titer in LK cells than in LFBK-$\alpha_v\beta_6$ cells. Infection with bluetongue virus (BTV) only induced cytopathic effects in IB-RS-2 and LK cells by 96 HPI.

TABLE 4

Growth of selected animal-derived vesicular disease viruses.

| | Cell Types | | | | |
|---|---|---|---|---|---|
| Virus | LFBK | LFBK-$\alpha_v\beta_6$ | IB-RS-2 | BHK | LK |
| VESV A48 ET 305 | 6.15[a] | 6.55 | 5.8 | ND[b] | 3.05 |
| SVDV UKG72 | 6.2 | 6.2 | 6.3 | ND | 3.05 |
| BSPV New York 2004 | 3.2 | 3.05 | 3.2 | ND | 3.8 |
| BTV-1 South Africa 1993 | ND | ND | 3.2 | ND | 3.05 |
| VSV New Jersey[c] | 7.3 | 7.05 | 6.55 | 6.3 | 5.8 |

[a]Virus titers in $\log_{10}TCID_{50}$/ml.
[b]ND, not detected. Limit of detection in this assay is 1.8 $\log_{10}TCID_{50}$/ml.
[c]This virus obtained from a pool of experimentally infected animal tissues.

Thus, LFBK$\alpha$v$\beta$6 cells can support the growth of VESV, SVDV, VSV-NJ and BPSV) as well or better than LFBK, IB-RS-2, BHK and LK.

The LFBK$\alpha$v$\beta$6 cell line has been deposited with the American Type Culture Collection (ATCC), 10801 University Blvd., Manassas, Va. 20110-2209 on Jul. 11, 2012, under accession number PTA-13047, as a patent deposit under the Budapest Treaty on the International Recognition of the Deposit of Microorganisms for the Purposes of Patent Procedure. The subject cell line has been deposited under conditions that assure that access to the cell line will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A stably transduced fetal porcine kidney cell line which has been engineered to express a functional bovine $\alpha_v\beta_6$ integrin receptor, said cell line comprising a host cell transduced with a heterologous nucleic acid molecule comprising a sequence of nucleotides that constitutively express an $\alpha_v$ subunit of the bovine $\alpha_v\beta_6$ integrin receptor and a sequence of nucleotides that constitutively express a $\beta_6$ subunit of the bovine $\alpha_v\beta_6$ integrin receptor, wherein said $\alpha_v$ subunit and said $\beta_6$ subunit comprise a sequence of nucleotides which encode the bovine $\alpha_v$ subunit and the bovine $\beta_6$ subunit of the bovine $\alpha_v\beta_6$ integrin receptor, a functional Foot and Mouth Disease Virus (FMDV) receptor wherein said cell line is the LFBKαvβ6 cell line deposited as ATCC Accession No: PTA-13047.

2. A transgenic fetal porcine kidney cell line expressing the bovine $\alpha_v\beta_6$ integrin receptor, obtained by a method comprising: a) transducing transformed fetal porcine kidney cells of the transformed LFBK cell line with a vector comprising a sequence that constitutively express an $\alpha_v$ subunit of the bovine $\alpha_v\beta_6$ integrin receptor; b) contacting the resulting transduced LFBK cells with a selection medium; and c) obtaining transduced LFBKα$_v$ cells, d) transducing said LFBKα$_v$ cells with a vector comprising a sequence that constitutively express a $\beta_6$ subunit of the bovine $\alpha_v\beta_6$ integrin receptor: e) selecting transduced LFBKα$_v$β$_6$ cells to obtain a stable transgenic LFBKα$_v$β$_6$ cell line, wherein said LFBKα$_v$β$_6$ cells show consistent expression of $\alpha_v$ and $\beta_6$ subunits as measured by immunohistochemistry and wherein said LFBKα$_v$β$_3$ cells show increased sensitivity for detection of all seven FMDV subtypes compared to a control LFBK cell line lacking constitutive stable expression of said $\alpha_v$ and $\beta_6$ subunits of said porcine LFBKα$_v$β$_6$ cells, wherein said cell line is the LFBKαvβ6 cell line deposited as ATCC Accession No: PTA-13047.

3. A method for producing any one or more of seven FMDV serotypes, comprising: a) providing i) a sample containing an FMDV; and ii) a composition comprising culture medium and a cell of the transgenic LFBKα$_v$β$_6$ cell line of claim 1 or claim 2; and b) inoculating said cell with said sample to produce an inoculated cell, wherein said inoculated cell produces said FMDV.

4. The method of claim 3 wherein any one or more of seven serotypes of FMDV are produced.

5. A method for detection of a Vesicular Disease-causing Virus in a sample, comprising: a) providing i) a sample; and ii) a composition comprising culture medium and a cell of the transgenic LFBKα$_v$β$_6$ cell line of claim 1 or claim 2; b) inoculating said cell with said sample to produce an inoculated cell; and c) observing said inoculated cell for the presence of said Vesicular Disease-causing Virus.

6. The method of claim 5, wherein said Vesicular Disease-causing Virus is one or more of vesicular exanthema of swine virus (VESV), swine vesicular disease virus (SVDV), vesicular stomatitis virus serotype New Jersey (VSV-NJ), or bovine popular stomatitis virus (BPSV).

7. A method for producing a Vesicular Disease-causing Virus, comprising: a) providing i) a sample containing a Vesicular Disease-causing Virus; and ii) a composition comprising culture medium and a cell of a the transgenic LFBKα$_v$β$_6$ cell line of claim 1 or claim 2; and b) inoculating said cell with said sample to produce an inoculated cell, wherein said inoculated cell produces said Vesicular Disease-causing Virus.

8. The method of claim 7, wherein said Vesicular Disease-causing Virus is one or more of vesicular exanthema of swine virus (VESV), swine vesicular disease virus (SVDV), vesicular stomatitis virus serotype New Jersey (VSV-NJ), or bovine popular stomatitis virus (BPSV).

9. A method for the detection and for the isolation and serological characterization of any one or more of seven FMDV serotypes in a sample, comprising: a) providing i) a sample; and ii) a composition comprising culture medium and a cell of the transgenic LFBKα$_v$β$_6$ cell line of claim 1 or claim 2; b) inoculating said cell with said sample to produce an inoculated cell; and c) observing said inoculated cell for the presence of said FMDV serotype or subtype.

10. The method of claim 9 wherein the presence of said FMDV is determined by the observation of visible cytopathic effects (CPE).

11. The method of claim 9 wherein any one or more of seven serotypes of FMDV are detected.

* * * * *